United States Patent [19]
Brodasky et al.

[11] Patent Number: 4,595,770
[45] Date of Patent: Jun. 17, 1986

[54] ANTIBIOTIC COMPOUND AND PROCESS FOR RECOVERY THEREOF FROM A FERMENTATION BROTH

[75] Inventors: Thomas F. Brodasky, Oshtemo Township, Kalamazoo County, Mich.; David W. Stroman, Bartlesville, Okla.

[73] Assignee: The Upjohn Company, Kalamazoo, Mich.

[21] Appl. No.: 390,093

[22] Filed: Jun. 21, 1982

[51] Int. Cl.$^4$ .................................. C07D 303/48
[52] U.S. Cl. .................................. 549/541; 549/546
[58] Field of Search ............... 542/420; 549/546, 541

[56] References Cited
U.S. PATENT DOCUMENTS 3,869,346  3/1975  Vezina et al. ................... 424/123
4,226,879  10/1980 Omura et al. ................... 542/420
4,335,108  6/1982  Argoudelis et al. ............. 424/123

FOREIGN PATENT DOCUMENTS 2253031  9/1973  Fed. Rep. of Germany ...... 424/122
754010   8/1956  United Kingdom ................. 424/123

OTHER PUBLICATIONS

K. Kakinuma et al., Jour. Am. Chem. Soc. (1979) 101:12, pp. 3402–3404.

Primary Examiner—Norma S. Milestone
Attorney, Agent, or Firm—Roman Saliwanchik; Joan Thierstein; Sidney B. Williams, Jr.

[57] ABSTRACT

Novel antibiotic U-56,407 producible in a fermentation under controlled conditions using a biologically pure culture of the microorganism *Streptomyces hagronensis* strain 360, NRRL 15064. This antibiotic is active against various Gram-positive bacteria, for example, *Staphylococcus aureus*, *Streptococcus pyogenes* and *Streptococcus pneumoniae*. Thus, antibiotic U-56,407 can be used in various environments to eradicate or control such bacteria.

3 Claims, 2 Drawing Figures

ANTIBIOTIC COMPOUND AND PROCESS FOR RECOVERY THEREOF FROM A FERMENTATION BROTH

BRIEF SUMMARY OF THE INVENTION

Antibiotic U-56,407 is producible in a fermentation under controlled conditions using a biologically pure culture of the new microorganism *Streptomyces hagronensis* strain 360, NRRL 15064.

Antibiotic U-56,407 is an acidic compound which is active against various Gram-positive bacteria. Thus, antibiotic U-56,407 can be used to disinfect washed and stacked food utensils contaminated with *S. aureus*. It can also be used as a disinfectant on various dental and medical equipment contaminated with *S. aureus*. Still further, antibiotic U-56,407 can be used as a bacteriostatic rinse for laundered clothes, and for impregnating papers and fabrics; and it is also useful for suppressing the growth of sensitive organisms in plate assays and other microbiological media.

DETAILED DESCRIPTION OF THE INVENTION

Chemical and Physical Properties of Antibiotic U-56,407

Equivalent Weight: 519.

Elemental Analysis: C, 66.28; H, 6.23; N, 5.49; O, 22.0.

Color of Pure Solid: Yellow.

Molecular Formula: $C_{29}H_{32}N_2O_7$; molecular weight calc. (520); Found FD (Field Description) mass spectrometry (521, M+1).

Melting Point: ca. 150°(dec.).

Infrared Absorption Spectrum: Antibiotic U-56,407 has a characteristic infrared absorption spectrum in mineral oil mull as shown in FIG. 1 of the drawings. Peaks are observed at the following wavelengths.

| Band Freq.[1] | Inten.[2] | Band Freq. | Inten. |
|---|---|---|---|
| 3550 | M | 1240 | M |
| 3450 | sh, M | 1190 | M |
| 3310 | S | 1166 | M |
| 3060 | M | 1150 | M |
| 3020 | M | 1130 | M |
| 2950 | S | 1102 | M |
| 2920 | S | 1075 | W |
| 2850 | S | 1060 | M |
| 2660 | W | 1037 | M |
| 1892 | W | 1002 | S |
| 1725 | sh, M | 980 | M |
| 1695 | S | 923 | W |
| 1667 | S | 880 | M |
| 1625 | S | 852 | W |
| 1610 | S | 825 | W |
| 1593 | sh, S | 805 | W |
| 1542 | S | 773 | W |
| 1525 | S | 735 | W |
| 1468 | M | 721 | W |
| 1435 | sh, M | 687 | M |
| 1373 | S | 655 | M |
| 1327 | M | | |
| 1262 | M | | |

[1]Wave numbers (cm$^{-1}$)
[2]S = Strong
M = Medium
W = Weak
sh = shoulder $^{13}$C-Nuclear Magnetic Resonance (NMR) Spectrum:

The $^{13}$C-NMR spectrum of antibiotic U-56,407 is shown in FIG. 2 of the drawings. The $^{13}$C-NMR spectrum was observed on a Varian CFT-80 Spectrometer in a solution (ca. 0.3 ml., ca. 150 mg/ml) of the sample of the antibiotic in deutero chloroform (CDCl$_3$). The spectrum was calibrated against tetramethylsilane and frequencies were recorded in ppm downfield from tetramethylsilane. The spectrum for U-56,407 in comparison with the known antibiotic asukamycin (Jour. Antib., Vol. 29, No. 9, p. 876, 1976; JACS 101:12, p. 3402, 1979) is as follows:

C$^{13}$ CHEMICAL SHIFTS[1] MULTIPLICITIES FOR U-56,407 AND ASUKAMYCIN

| Carbon No. | U-56,407 | Asukamycin |
|---|---|---|
| 1 | 189.6 (s)[2] | 189.2 (s) |
| 2 | 128.2 (s) | 127.9 (s) |
| 3 | 130.1 (d) | 129.8 (d) |
| 4 | 70.8 (s) | 70.5 (s) |
| 5 | 56.6 (d) | 56.4 (d) |
| 6 | 52.6 (d) | 52.4 (d) |
| 7–12 | Unassigned | Unassigned |
| 13 | 166.1 (s) | 165.7 (s) |
| 1' | 165.0 (s) | 164.7 (s) |
| 2'–6' | Unassigned | Unassigned |
| 7' | 138.3 (d) | 144.7 (d) |
| 8' | 41.8 (t) | 40.2 (d) |
| 9' | 28.0 (d) | 28.6 (broad t) |
| 10', 11' | 22.3 (q) | |
| 1" | 198.0 (s) | 197.9 (s) |
| 2" | 115.0 (s) | 114.7 (s) |
| 3" | 175.8 (s) | 174.6 (s) |
| 4" | 25.5 (t) | 25.5 (t) |
| 5" | 32.2 (t) | 31.9 (t) |

Unassigned doublets:
U-56,407 - 142.3, 141.4, 140.4, 139.8, 139.4, 131.4, 131.4, 129.1, 128.4, 123.7, 122.5
Asukamycin - 142.0, 141.0, 140.4, 139.4, 139.0, 131.2, 128.8, 128.2, 127.4, 123.3, 122.2

[1]Relative to TMS
[2]s = singlet; d = doublet; t = triplet; q = quartet

Solubilities

Antibiotic U-56,407 is soluble in halogenated hydrocarbons and alcohols; it is not soluble in hydrocarbons or water.

Antimicrobial Spectrum of Antibiotic U-56,407:

Antibiotic U-56,407 is active against various Gram-positive bacteria as shown in the following table.

Assay Conditions: 80 mcl of 8 mg/ml methanolic solution of U-56,407 is applied to 12.5 mm paper discs and allowed to dry. The discs are then applied to the surface of seeded agar trays and incubated at the designated temperature for a period of 16 hours. The zones of inhibition are then read to the nearest mm.

| Organism | Zone of Inhibition (mm) |
|---|---|
| *Bacillus subtilis* UC 564 | 24 |
| *Bacillus subtilis* UC 6033 (Amicetin resistant) | 27 |
| *Staphylococcus aureus* UC 80 | 24 |
| *Staphylococcus aureus* UC 3665 (Macrolide resistant) | 21 |
| *Staphylococcus aureus* UC 6029 (Streptomycin resistant) | 19 |
| *Sarcina lutea* UC 130 | 17 |
| *Sarcina lutea* UC 3383 (Erythromycin resistant) | 22 |
| *Sarcina lutea* sens. UC 130 (plt 8.3) | 22 |
| *Klebsiella pneumoniae* UC 57 | 0 |
| *Escherichia coli* UC 51 | 0 |
| *Salmonella schottmuelleri* UC 126 | 0 |

-continued

| Organism | Zone of Inhibition (mm) |
|---|---|
| *Proteus vulgaris* UC 93 | 0 |
| *Myobacterium avium* UC 159 | 16 |
| *Penicillium oxalicum* UC 1268 | 18 (hazy) |
| *Saccharomyces pastorianus* UC 1342 | 0 |
| *Pseudomonas aeruginosa* UC 95 | 0 |
| *Rhodopseudomonas spheroides* UC 3238 | 15 |
| *Streptococcus pyogenes* UC 152 | 22 |
| *Clostridium perfringens* UC 6509 | 23 |
| *Bacteroides fragilis* UC 6513 | 24 |

"UC" is a registered trademark of The Upjohn Company Culture Collection.

THE MICROORGANISM

Figure 1:
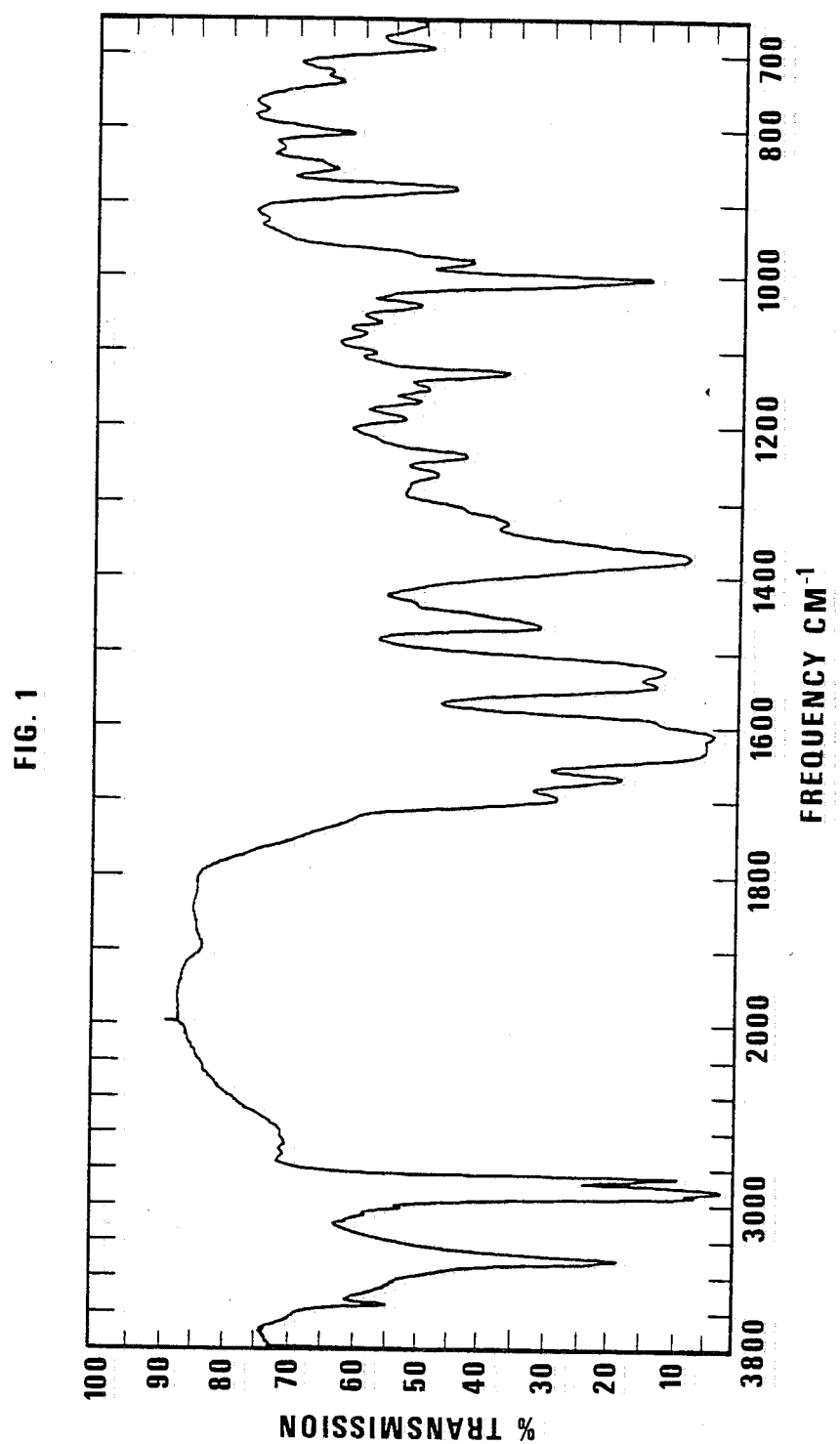
FIG. 1—Infrared absorption spectrum of antibiotic U-56,407.
Figure 2:
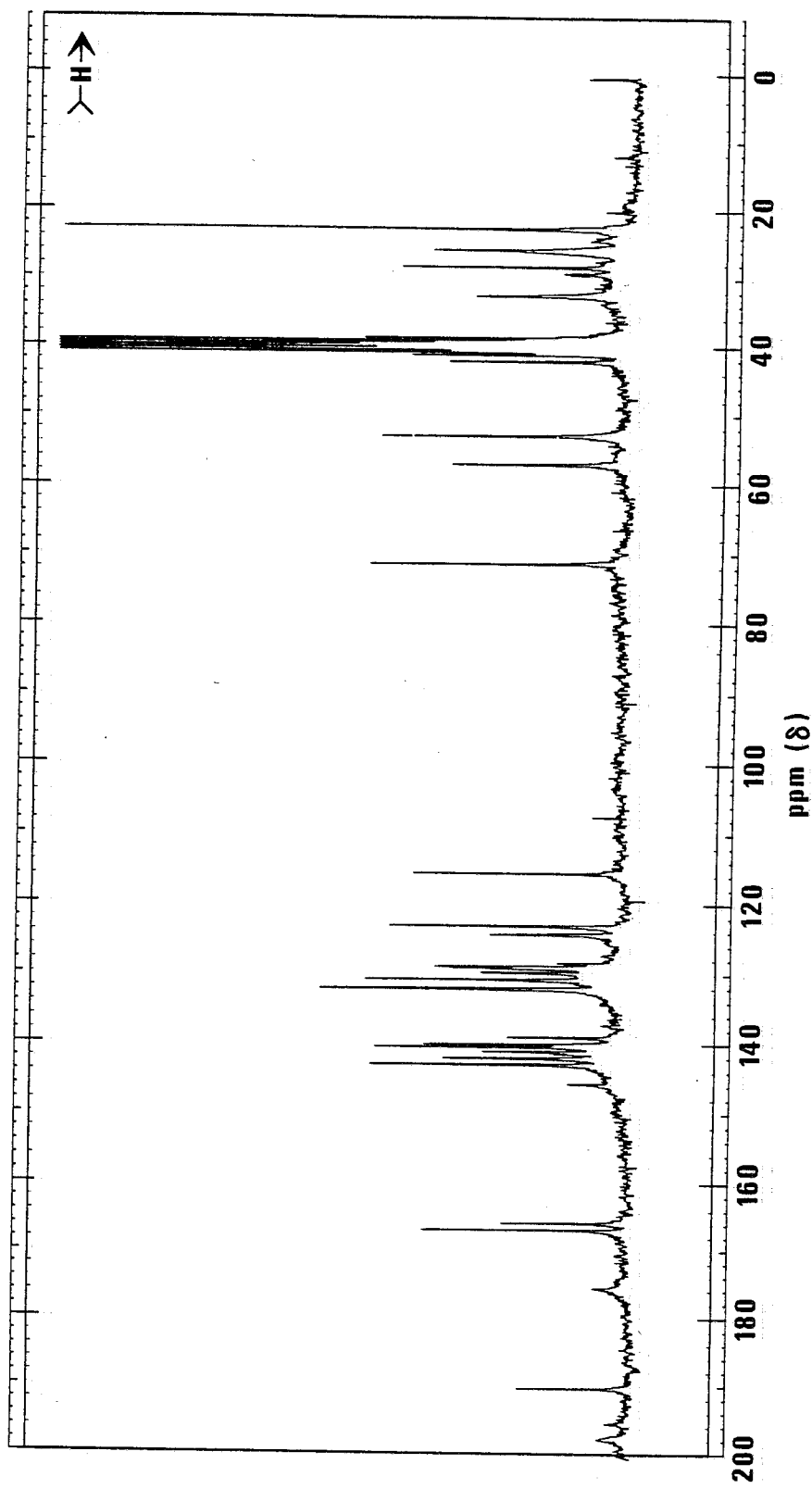
FIG. 2—$^{13}$C-Nuclear Magnetic Resonance (NMR) spectrum of antibiotic U-56,407.

The microorganism used for the production of antibiotic U-56,407 is a biologically pure culture of *Streptomyces hagronensis* strain 360, NRRL 15064.

A subculture of this microorganism can be obtained from the permanent collection of the Northern Regional Research Laboratory, U.S. Department of Agriculture, Peoria, Ill., U.S.A. A viable subculture was deposited on May 27, 1982. Its accession number in this depository is NRRL 15064. It should be understood that the availability of the culture does not constitute a license to practice the invention in derogation of patent rights granted with the subject instrument by governmental action.

The microorganism of this invention was studied and characterized by Alma Dietz and Grace P. Li of The Upjohn Research Laboratories. *Streptomyces hagronensis* strain 360, NRRL 15064.

Color Characteristics: Aerial growth gray. Melanin negative. Color comparisons with *Streptomyces lemensis* (1) are given in Table 1 (Appearance on Ektachrome) and Table 2 (Reference color characteristics). The new culture may be placed in the Gray (GY) color series of Tresner and Backus [Tresner, H. D., and E. J. Backus, 1963. System of color wheels for streptomycete taxonomy. Appl. Microbiol. 11:335-338]; *S. lemensis* may be placed in their Red (R) or Gray (GY) color groups.

Microscopic Characteristics: Spore chains long, open spiraled to spiral. Spores appressed. Spore surface smooth with constrictions when observed with the scanning microscope by the procedure of Dietz and Mathews [Dietz, A., and J. Mathews. 1971. Classification of Streptomyces spore surfaces into five groups. Appl. Microbiol. 21:527-533].

Growth on Carbon Compounds: See Table 3.

General Cultural Characteristics: See Table 4.

Temperature: Both cultures grow in the temperature range of 18C-37C on Bennett's, Czapek's sucrose, maltose-tryptone, and yeast extract-malt extract (ISP-2) agars. *S. lemensis* had poor vegetative growth at 45C; the new culture did not grow at 45C.

Whole Cell Analysis: *S. hagronensis* strain 360 and *S. lemensis* contained L-diaminopimelic acid.

Source: Soil sample from Washington.

*Streptomyces hagronensis* strain 360, NRRL, 15064, is differentiated from *Streptomyces lemensis*, the culture in our collection to which it appeared most similar in its color pattern on Ektachrome and in its microscopic characteristics. *S. hagronensis* strain 360 also produces the well-known antibiotic globomycin. Five cultures are reported in the literature [Inukai, M., R. Enokita, A. Torikata, M. Nakahara, S. Iwado, and M. Arai. 1978. Globomycin, a new peptide antibiotic with spheroplast-forming activity. J. Antibiotics. 31:410-420; and Omoto, S., H. Suzuki, and S. Inouye. 1979. Isolation and structure of SF-1902 A5, a new globomycin analogue. J. Antibiotics 32:83-86] as producers of globomycin. Four of the cultures: *Streptomyces halstedii*, *Streptomyces hygroscopicus*, *Streptomyces neohygroscopicus* subsp. *globomyceticus*, and *Streptoverticillium cinnamomeum* cannot be considered similar to the new culture because the type strains of these cultures are distinguishable from it on Ektachrome and in microscopic characteristics. Characteristics cited for the fifth culture, *Streptomyces hagronensis*, indicated some similarity to the new culture. The data reported for observation of *S. hagronensis* on media that we use, as noted in Tables 2-4, indicate a strong similarity of the new culture to *S. hagronensis*. In addition, *S. hagronensis* has open spiral to spiral chains of smooth spores. The most significant differences are in growth on D-xylose (strongly positive for the new culture; negative for *S. hagronensis*) and on rhamnose (positive for the new culture and negative for *S. hagronensis*). Although there is a strong similarity of the new culture to *S. lemensis* on Ektachrome and microscopically (there are differences between the cultures in growth on carbon compounds (Table 3) and in gelatin liquefaction), *S. lemensis* has not been reported to produce globomycin. Therefore, we consider the new isolate to be most similar to *S. hagronensis*. In accordance with the rules set forth in the International Code of Nomenclature of Bacteria [Lapage, S. P., P. H. A. Sneath, E. F. Lessel, V. B. D. Skerman, H. P. R. Seeliger, and W. A. Clark, eds. 1975. International code of nomenclature of bacteria, 1976 Revision. American Soceity for Microbiology, Washington, D.C.], we propose that the new culture be designated *Streptomyces hagronensis* strain 360. We further propose that the type strain *Streptomyces hagronensis* be designated the type subspecies, *Streptomyces hagronensis* subsp. *hagronensis*.

TABLE 1

Color Characteristics* on Ektachrome[1, 2]

| Agar Medium | Determination | S. hagronensis strain 360 NRRL 15064 Chip | Color | S. lemensis NRRL 8170 Chip | Color |
|---|---|---|---|---|---|
| Bennett's | S | 22 | reddish gray | 22 | reddish gray |
|  | R | 55 | strong brown | 54 | brownish orange |
| Czapek's | S | 10 | pinkish gray | 8 | grayish pink |
| sucrose | R | 93 | yellowish gray | 93 | yellowish gray |
| Maltose- | S | 22 | reddish gray | 22 | reddish gray |
| tryptone | R | 54 | brownish orange | 54 | brownish orange |
| Peptone- | S | 71 | moderate orange-yellow | 71 | moderate orange-yellow |
| iron | R | 68 | strong orange-yellow | 68 | strong orange-yellow |
| 0.1% | S | 68 | strong orange-yellow | 89 | pale yellow |
| Tyrosine | R | 67 | brilliant orange-yellow | 89 | pale yellow |
| Casein | S | 10 | pinkish gray | 8 | grayish-pink |

TABLE 1-continued

Color Characteristics* on Ektachrome[1, 2]

| Agar Medium | Determination | S. hagronensis strain 360 NRRL 15064 Chip | S. hagronensis strain 360 NRRL 15064 Color | S. lemensis NRRL 8170 Chip | S. lemensis NRRL 8170 Color |
|---|---|---|---|---|---|
| starch | R | 93 | yellowish gray | 93 | yellowish gray |

S = Surface
R = Reverse

[1]Dietz, A. 1954. Ektachrome transparencies as aids in actinomycete classification. Ann. N.Y. Acad. Sci. 60:152–154
[2]Dietz, A. and D. W. Thayer (ed.). 1980. Actinomycete Taxonomy (Procedures for Studying Aerobic Actinomycetes with Emphasis on the Streptomycetes). SIM Special Publication Number 6. Soc. for Ind. Microbiol., Arlington, VA.
*Growth on media in tubes was photographed after seven days incubation at 28° C. Color was determined by comparison with NBS color chips [SP 440. Color: Universal Language and Dictionary of Names. U.S. Government Printing Office, Washington, D.C. 20402.]; and [SRM 2106. ISCC-NBS Centroid Color Charts. Office of Standard Reference Material, Room B311, Chem. Building, National Bureau of Standards, Washington, D.C. 20234].

TABLE 3

Growth on Carbon Compounds in the Synthetic Medium of Shirling and Gottlieb*

| Synthetic Agar (ISP-9) | S. hagronensis strain 360 NRRL 15064 | S. lemensis NRRL 8170 | S. hagronensis No. 17834 |
|---|---|---|---|
| Control - Negative (No carbon compound) | + (very light growth) | + (very light growth) | − |
| Control - Positive (D-glucose) | ++ | ++ | + |
| L-arabinose | − | + | − |
| Sucrose | ± | − | − |
| D-xylose | ++ | + | − |
| Inositol | − | − | − |
| D-mannitol | − | ++ | − |
| D-fructose | ± | + | ± |
| Rhamnose | + | − | − |
| Raffinose | + | ± | ± |
| Cellulose | − | − | − |

++ = Strong utilization
+ = Positive utilization
± = Doubtful utilization
− = No utilization
*Shirling and Gottlieb, supra.

TABLE 2

Reference Color Characteristics*

| Agar Medium | Determination | S. hagronensis strain 360 NRRL 15064 | | S. lemensis NRRL 8170 | | S. hagronensis No. 17834 | |
|---|---|---|---|---|---|---|---|
| Bennett's | S | 33 | brownish pink | 42 | light reddish brown | | |
| | R | 59 | dark brown | 56 | deep brown | | |
| | P | 75 | deep yellowish brown | 75 | deep yellow-brown | | |
| Czapek's sucrose | S | 33 | brownish pink | 42 | light reddish brown | | |
| | R | 33 | brownish pink | 42 | light reddish brown | | |
| | P | — | — | — | — | | |
| Maltose-tryptone | S | 60 | light grayish brown | 42 | light reddish brown | | |
| | R | 59 | dark brown | 54 | brownish orange | | |
| | P | 78 | dark yellowish brown | 32 | grayish yellowish pink | | |
| Yeast extract-malt extract (ISP-2) | S | 60 | light grayish brown | 42 | light reddish brown | 2-7-8 | light brownish gray |
| | R | 59 | dark brown | 55 | strong brown | 6-5-8 | yellowish brown |
| | P | 78 | dark yellowish brown | — | — | — | dull yellow |
| Oatmeal (ISP-3) | S | 33 | brownish pink | 42 | light reddish brown | 2-7-9 | pale yellowish brown |
| | R | 75 | deep yellowish brown | 76 | light yellowish brown | 4-4-9 | dark yellowish brown |
| | P | 90 | grayish yellow | — | — | 4-7-9 | yellowish brown |
| Inorganic Salts-Starch (ISP-4) | S | 60 | light grayish brown | 42 | light reddish brown | 2-6-7 | grayish brown |
| | R | 75 | deep yellowish brown | 71 | moderate orange yellow | 3-3-8 | dark yellowish brown |
| | P | 75 | deep yellowish brown | 75 | deep yellowish brown | — | — |
| Glycerol-asparagine (ISP-5) | S | 60 | light grayish brown | 42 | light reddish brown | 2-7-8 | light brownish gray |
| | R | 59 | dark brown | 57 | light brown | 6-6-9 | yellowish brown |
| | P | 78 | dark yellowish brown | 57 | light brown | — | pale yellow |

S = Surface
R = Reverse
P = Pigment
*Color determination was made on growth on plates incubated 14 days at 28° C. Color was determined by comparison with NBS color chips [SP 440, supra] and [SRM 2106, supra].

TABLE 4

Culture Characteristics - General

| Medium | Determination | S. hagronensis strain 360 NRRL 15064 | S. lemensis NRRL 8170 | S. hagronensis No. 17834 |
|---|---|---|---|---|
| Agar | | | | |
| Peptone-iron | S | — | — | |
| | R | Colorless to yellow-tan | Colorless to yellow-tan | |
| | P | — | — | |
| | O | Melanin-negative | Melanin-negative | |
| Calcium malate | S | — | — | |
| | R | Pale cream | Colorless | |
| | P | — | — | |
| | O | Malate not solubilized | Malate not solubilized | |
| Glucose-asparagine | S | Trace pale gray | Trace pale gray pink | Light brownish gray |
| | R | Cream-tan | Yellow | Yellowish brown |
| | P | Pink-tan | — | — |
| Skim milk | S | — | — | |
| | R | Orange | Pale orange | |
| | P | Orange | Pale orange | |
| | O | Casein solubilized | Casein slightly solubilized | |
| Tyrosine | S | — | Pale pink | |
| | R | Tan | Yellow | |
| | P | Tan | Pale yellow | |
| | O | Tyrosine solubilized | Tyrosine solubilized | |
| Xanthine | S | — | Pale pink | |
| | R | Colorless | Yellow | |
| | P | — | Pale yellow | |
| | O | Xanthine solubilized | Xanthine solubilized | |
| Nutrient starch | S | — | Pale pink | |
| | R | Colorless | Yellow | |
| | P | — | Pale yellow | |
| | O | Starch hydrolyzed | Starch hydrolyzed | Starch hydrolyzed |
| Yeast extract-malt extract | S | Trace gray | Gray pink | |
| | R | Tan | Pink-tan | |
| | P | Tan | Pink-tan | |
| Peptone-yeast extract-iron (ISP-6) | S | Colorless | Colorless | |
| | R | Colorless to yellow tan | Colorless to yellow tan | |
| | O | Melanin negative | Melanin negative | Melanin negative |
| Tyrosine (ISP-7) | S | Gray with trace black exudate | Gray-pink | |
| | R | Light brown | Pale rose | |
| | O | Melanin negative | Pale rose pigment; Melanin negative | Tyrosinase negative |
| Gelatin | | | | |
| Plain | S | Colorless vegetative growth | Colorless vegetative growth | |
| | P | — | — | |
| | O | Liquefaction ½ | Trace liquefaction | |
| Nutrient | S | Colorless vegetative | Gray aerial | |
| | P | — | Very pale tan | |
| | O | Liquefaction ½ | Trace liquefaction | Liquefaction |
| Broth | | | | |
| Synthetic nitrate | S | — | — | |
| | P | — | — | |
| | O | Compact pale tan bottom growth | Colorless very fine growth clinging to wall of tube | |
| | | Nitrates reduced to nitrites | Nitrates reduced to nitrites | |
| Nutrient nitrate | S | — | White aerial growth on surface pellicle | |
| | P | — | — | |
| | O | Flocculent yellow bottom growth | Flocculent colorless bottom growth | |
| | | Nitrates reduced to nitrites | Nitrates not reduced | Nitrates not reduced |
| Litmus | S | Blue-gray surface ring | Gray aerial growth on surface ring | |
| | P | Purple | Purple | |
| | O | Peptonization | Peptonization | Peptonization |

TABLE 4-continued

| Medium | Deter-mination | Culture Characteristics - General | | |
| --- | --- | --- | --- | --- |
| | | S. hagronensis strain 360 NRRL 15064 | S. lemensis NRRL 8170 | S. hagronensis No. 17834 |
| | pH | 7.5 | 7.3 | 7.6 |

S = Surface (aerial growth unless otherwise noted)
R = Reverse
P = Pigment
O = Other characteristics The compound of the invention process is produced when the elaborating organism is grown in an aqueous nutrient medium under submerged aerobic conditions. It is to be understood, also, that for the preparation of limited amounts surface cultures and bottles can be employed. The organism is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distiller's solids, animal peptone liquors, meat and bone scraps, and the like. Combinations of these carbon and nitrogen sources can be used advantageously.

Production of the compound by the invention process can be effected at any temperature conducive to satisfactory growth of the microorganism, for example, between about 18° and 40° C., and preferably between about 20° and 28° C. Ordinarily, optimum production of the compound is obtained in about 2 to 15 days. The medium normally remains alkaline during the fermentation. The final pH is dependent, in part, on the buffers present, if any, and in part on the initial pH of the culture medium.

When growth is carried out in large vessels and tanks, it is preferable to use the vegetative form, rather than the spore form, of the microorganism for inoculation to avoid a pronounced lag in the production of the compound and the attendant inefficient utilization of the equipment. Accordingly, it is desirable to produce a vegetative inoculum in a nutrient broth culture by inoculating this broth culture with an aliquot from a soil, liquid $N_2$ agar plug, or a slant culture. When a young, active vegetative inoculum has thus been secured, it is transferred aseptically to large vessels or tanks. The medium in which the vegetative inoculum is produced can be the same as, or different from, that utilized for the production of the compound, so long as a good growth of the microorganism is obtained.

A variety of procedures can be employed in the isolation and purification of the compound produced by the subject invention from fermentation beers. Isolation can be accomplished by solvent extraction, and adsorption on non-ionic macroporous resins. Chromatography on silica gel can be used to purify crude preparations of the antibiotic.

In a preferred recovery process, the compound produced by the subject process is recovered from the culture medium by mixing the whole fermentation broth with a chlorinated hydrocarbon solvent, for example, methylene chloride. Diatomaceous earth, for example Dicalite, is added to this mixture and, after mixing thoroughly, the broth is filtered. The cake is washed with the chlorinated hydrocarbon used above and this washing is combined with the original filtrate wherein resides the desired antibiotic. This material can be evaporated down and the crude antibiotic precipitated from the resulting residue by mixing with an appropriate solvent, for example, hexane. The precipitate can be washed several times with hexane and dried to yield a crude preparation of antibiotic U-56,407.

Alternatively, the antibiotic can be recovered from the fermentation broth by separation of the mycelia and undissolved solids by conventional means, such as by filtration or centrifugation, and resin adsorption of the filtered broth. The antibiotic of the subject invention can be recovered from the filtered beer by resin sorption on a resin comprising a non-ionic macroporous copolymer of styrene cross-linked with divinylbenzene. Suitable resins are Amberlite XAD-2 and XAD-4, according to the procedure disclosed in U.S. Pat. No. 3,515,717. (Amberlite resins are available from Rohm and Haas, Philadelphia, PA.). The antibiotic can be eluted from said resins by using acetone.

Resins other than XAD-2 and XAD-4 may be substituted. Charcoal can also be used. Extraction with a solvent like 1-butanol also can be used.

The eluting solvent from the resins will vary from resin to resin. A combination of water and acetone (10:90 v/v) can be used.

Purification of the antibiotic from the resin eluate can be done by chromatography on silica gel and subsequent crystallization from methanol.

Base addition salts, e.g. metal salts, for example, sodium, calcium, magnesium and potassium; and other salts, for example, ammonium and triethyl ammonium of antibiotic U-56,407 can be made by use of standard procedures. These salts can be used for the same purposes as the parent antibiotic.

The following examples are illustrative of the process and product of the invention, but are not to be construed as limiting. All percentages are by weight and all solvent mixture proportions are by volume unless otherwise noted.

EXAMPLE 1

A. Fermentation

A biologically pure culture of Streptomyces hagronensis strain 360, NRRL 15064, is used to inoculate 500-ml. Erlenmeyer seed flasks containing 100 ml of sterile medium consisting of the following ingredients:

| | g/liter |
| --- | --- |
| Glycerol | 10.0 |
| Difco peptone | 10.0 |
| Difco yeast extract | 10.0 |
| Tap water q.s. to 1 liter. | | pH is adjusted to 7.0 with KOH before sterilization. Lard oil (1 ml/l) is added as an antifoaming agent.

The seed inoculum is grown for three days at 28° C. on a Gump rotary shaker operating at 250 rpm and having a 2½ inch stroke.

Seed inoculum (5% seed), prepared as described above, is used to inoculate 500-ml Erlenmeyer flasks containing 100 l. of the following sterile medium:

|  | g/liter |
| --- | --- |
| Corn gluten meal | 20.0 |
| Starch | 10.0 |
| Glycerol | 20.0 |
| CaCO$_3$ | 2.0 |
| Tap water q.s. to 1 liter. |  | pH is adjusted to 7.5 with KOH before sterilization. The inoculated fermentation medium is incubated at a temperature of 28° C. for 7 days on a Gump rotary shaker as described above.

A typical seven-day fermenation has the following titers of antibiotic in the fermentation broth using a standard broth dilution assay:

| Day | Assay, S. aureus (BU/ml) |
| --- | --- |
| 1 | 0 |
| 2 | 4.0 |
| 3 | 6.0 |
| 4 | 4.0 |
| 7 | 0 |

A BU (biounit) is the concentration of the antibiotic which gives a 20 mm zone of inhibition against the test organism.

B. Recovery

To whole beer from a fermentation, as described above, is stirred one volume of CH$_2$Cl$_2$. To this mixture is added 20% (w/v) of Dicalite and after thoroughly mixing, the broth is filtered. The cake is washed with ½ beer vol. of CH$_2$Cl$_2$ and the wash is combined with the original filtrate. The extract is dried with a suitable drying agent (Na$_2$SO$_4$) and evaporated at less than 40° C. under vacuum. The oily residue which results is dissolved in 92.5% CH$_2$Cl$_2$:7.5% MeOH in a ratio of 3:1 (v/v). This solution is mixed with 3 vols of hexane and stirred. The precipitate which forms is filtered off, washed several times with hexane and dried. The potency of this crude antibiotic preparation is determined by preparing a 1 mg/ml solution in methanol or chlorinated hyrocarbon solvent and making serial dilutions with the solvent to 0.125 mg/ml. After applying 80 mcl of the solution to 12.5 mm paper discs and drying, the discs are applied to the surface of agar seeded with S. aureus. Afte incubation of the seeded agar at 32° C., the zones of inhibition are read to the nearest mm and these values are used in a regression program to compute the biounits/mg, i.e. the dilution necessary to give 20 mm zone. The composition of this antibiotic preparation is determined by thin layer chromatography on silica gel (having in its composition a suitable phosphor) using 92.5% CHCl$_3$ or CH$_2$Cl$_2$:7.5% MeOH or 80% THF:20% cyclohexane. The plates are visualized by 254 nm light or by bioautography on S. aureus seeded agar. U-56407 has an R$_f$ value of 0.45 in the CHCl$_3$:MeOH mobile phase and 0.55 in the THF:cyclohexane mobile phase.

C. Purification

Crude preparations of U-56,407, prepared as described above, can be purified by chromatography on silica gel and subsequent crystallization from methanol.

A column is wet packed with 100 g silica gel per gram of U-56,407 crude prep to be processed using a mobile phase composed of the following solvents: CHCl$_3$ or CH$_2$Cl$_2$ 9.25% MeOH 7.5%. A charge of crude U-56,407 is prepared by mixing the solid with two times its weight of silica gel in the mobile phase described above and evaporating off the solvent. The dry powder is charged onto the head of the column after it has settled. The column is eluted with the above mobile phase at the rate of 8–10 ml/min (0.1–0.2 cm/min linear velocity). Fractions (20 ml) are collected and every 5th fraction is bioautographed against S. aureus and K. pneumoniae. The fractions showing zones of inhibition against S. aureus but not K. pneumoniae are pooled. The solvent is evaporated from the fractions and the solid washed with hexane and filtered. The purity of this solid is assessed by bioautographic TLC using Q6 silica gel and the above mobile phase using S. aureus as a detecting organism on viewing the plates under 254 nm light. At this point the solid should not contain any other antibaterially active material. The solid from this column is then slurried with methanol (100 ml/g) and sufficient CHCl$_3$ added to effect a solution of the sample. This solution is allowed to stand at room temperature until crystallization of antibiotic U-56,407 occurs. The purity of the crystalline material can be ascertained by TLC on Q6F with the described mobile phase. Only a single fluorescence-quenching spot (under 254 nm light) should be observed. On subsequent bioautography of this material on Q6F TLC plates using a gram positive organism such as S. aureus, only a single zone of inhibition at R$_f$0.45 should be observed. In addition, the infrared spectrum of this material should be identical to that shown in FIG. 1 of the drawings.

Consideration of all of the physical-chemical data presented, and particularly comparison of these data with similar data for the antibiotic asukamycin [Journ. Antib., Vol. 29, No. 9, p. 876 (1976) and JACS 101:12, p. 3402 (1979)] supports the structure for U-56,407 as shown in Chart I. Whereas the UV spectrum, IR spectrum and C$^{13}$ NMR spectra of U-56,407 are consistent with the spectra for asukamycin, U-56,407 and asukamycin are differentiated on the basis of the following data:

|  | U-56,407 | Asukamycin |
| --- | --- | --- |
| mp | 150 (dec.) | 188 (dec.) |
| [α]$_D^{25}$(CHCl$_3$) | +263 | +181 |
| Mol. Wt. | 520 | 546 |
| Mol. Formula | C$_{29}$H$_{32}$N$_2$O$_7$ | C$_{31}$H$_{34}$N$_2$O$_7$ |

Inasmuch as the structures of U-56,407 and asukamycin differ at the C$_{8'}$ carbon atom, the C$^{13}$ NMR spectra allow differentiation of the two antibiotics.

CHART I

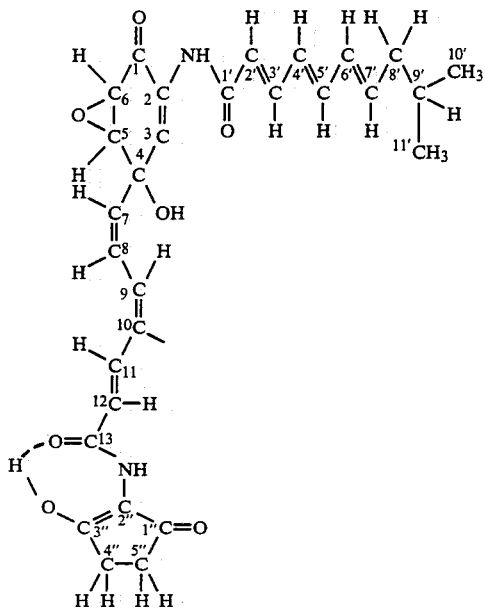

We claim:

1. A compound having the formula

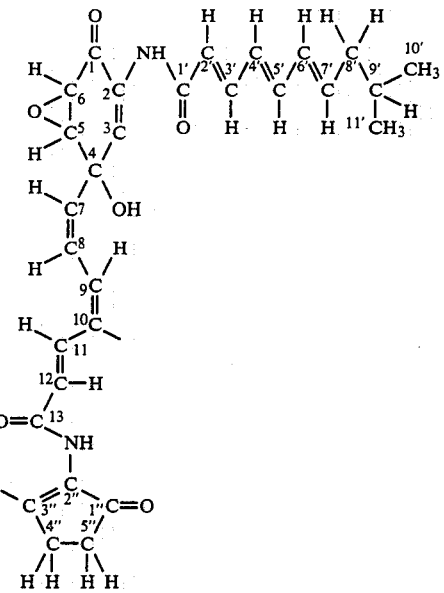

2. A process for recovering antibiotic U-56,407 from a fermentation broth obtained by cultivating *Streptomyces hagronensis* strain 360, having the identifying chracteristics of NRRL 15064, in an aqueous nutrient medium under aerobic conditions until substantial antibiotic U-56,407 activity is imparted to said medium, which comprises:
(a) mixing a chlorinated hydrocarbon solvent with the whole fermentation both;
(b) adding diatomaceous earth to the mixture of whole fermentation broth and chlorinated hydrocarbon solvent, mixing, and filtering to obtain a filtrate and cake;
(c) washing said cake and combining the wash with said filtrate; and
(d) recovering antibiotic U-56,407 from said combined wash and filtrate.

3. A process, according to claim 2, wherein said chlorinated hydrocarbon solvent is methylene chloride.

* * * * *

UNITED STATES PATENT OFFICE
CERTIFICATE OF CORRECTION

Patent No. 4,595,770                    Dated   June 17, 1986

Inventor(s)  T. F. Brodasky and D. W. Stroman

It is certified that error appears in the above-identified patent and that said Letters Patent are hereby corrected as shown below:

Column 12, line 10, "9.25%" should read --92.5%--
Column 14, line 34, "both" should read --broth--

Signed and Sealed this

Sixteenth Day of December, 1986

*Attest:*

DONALD J. QUIGG

*Attesting Officer*          *Commissioner of Patents and Trademarks*